US006600069B2

(12) United States Patent
Robinson et al.

(10) Patent No.: US 6,600,069 B2
(45) Date of Patent: Jul. 29, 2003

(54) BENZENE TRICARBOXYLIC ACID DERIVATIVES AS INSULIN RECEPTOR ACTIVATORS

(75) Inventors: Louise Robinson, San Carlos, CA (US); Prasad V. V. S. V. Manchem, South San Francisco, CA (US); Nicolas Cairns, Burlingame, CA (US); Steven R. Schow, Redwood Shores, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 09/949,165

(22) Filed: Sep. 6, 2001

(65) Prior Publication Data
US 2002/0103183 A1 Aug. 1, 2002

Related U.S. Application Data
(60) Provisional application No. 60/230,738, filed on Sep. 7, 2000.

(51) Int. Cl.[7] ..................... C07C 309/35; A61K 31/185
(52) U.S. Cl. .................. 562/54; 562/452; 562/453; 562/455; 562/573; 564/153; 514/381; 514/553; 514/563; 514/616; 514/674; 548/250
(58) Field of Search .......................... 564/153; 514/616, 514/563, 574, 553, 381; 562/452, 453, 455, 573, 54; 548/250

(56) References Cited

U.S. PATENT DOCUMENTS

| 4,046,805 A | 9/1977 | Bernstein et al. |
|---|---|---|
| 4,051,176 A | 9/1977 | Bernstein et al. |
| 4,089,974 A | 5/1978 | Conrow et al. |
| 4,102,917 A | 7/1978 | Conrow et al. |
| 4,118,585 A | 10/1978 | Conrow et al. |
| 4,120,891 A | 10/1978 | Poletto et al. |
| 4,120,895 A | 10/1978 | Conrow et al. |
| 4,123,455 A | 10/1978 | Conrow et al. |
| 4,129,591 A | 12/1978 | Bernstein et al. |
| 4,132,730 A | 1/1979 | Conrow et al. |
| 4,159,384 A | 6/1979 | Conrow et al. |
| 4,229,371 A * | 10/1980 | Conrow et al. |
| 5,750,573 A | 5/1998 | Bianchi et al. |
| 5,830,920 A | 11/1998 | Chucholowski et al. |
| 5,973,076 A | 10/1999 | Yoshimura et al. |

FOREIGN PATENT DOCUMENTS

| DE | 3327191 | 2/1984 |
|---|---|---|
| DE | 4229182 | 3/1994 |
| EP | 0 741 128 A2 | 4/1996 |
| EP | 0 940 431 A1 | 9/1999 |
| FR | 2 796 942 A1 | 2/2001 |
| WO | WO 96/14324 | 5/1996 |
| WO | WO 01/12591 A1 | 2/2001 |

OTHER PUBLICATIONS

Abstract for Japanese Patent No. 08333324, XP–002193996 Dec. 1996.
Abstract for Japanese Patent No. 09258359, XP–00219335, Oct. 1997.
Harris et al., "Ferric Ion Swquestering Agents. 6.[1] The Spectrophotometric Evaluation of Sulfonated Tricatecholate Ligands", *American Chemical Society*, 1981, vol. 103, No. 10, pp. 2667–2675.

* cited by examiner

Primary Examiner—Shailendra Kumar
(74) Attorney, Agent, or Firm—Heller Ehrman White & McAuliffe LLP

(57) ABSTRACT

Compounds of Formula I, and pharmaceutical compositions containing these compounds, activate the insulin receptor kinase, which leads to an increased sensitivity to insulin and an increase in glucose uptake, and are therefore useful for the treatment of animals, especially humans, with hyperglycemia, especially for the treatment of type 2 diabetes. Processes for preparation of the compounds, and their use in assays, are also disclosed.

35 Claims, No Drawings

BENZENE TRICARBOXYLIC ACID DERIVATIVES AS INSULIN RECEPTOR ACTIVATORS

CROSS-REFERENCE TO RELATED APPLICATION

This application claims the priority under 35 USC119(e) of US Provisional Application No. 60/230,738, filed Sep. 7, 2000.

BACKGROUND OF THE INVENTION (a) Field of the Invention

The present invention relates to chemical compounds, pharmaceutical compositions comprising said compounds, uses of said compounds and compositions, and processes for their preparation. Specifically, this invention relates to means to enhance insulin-dependent glucose uptake. More specifically, the invention concerns compounds and pharmaceutical compositions that activate the insulin receptor kinase, which leads to an increased sensitivity to insulin and an increase in glucose uptake, as well as processes for preparation of the compounds. As such, the invention also concerns methods or uses of the compounds for the treatment of animals with hyperglycemia, especially for the treatment of type 2 diabetes.

(b) Description of Related Art

High specificity interaction with receptors is among the many functions performed by peptide and protein hormones in metabolism. The insulin receptor-is present on virtually all cells and at high concentrations on the cells of the liver, skeletal muscle, and adipose tissue. Specific binding by insulin and resulting stimulation of the insulin receptor is an essential element in carbohydrate metabolism and storage.

Diabetics either lack sufficient endogenous secretion of the insulin hormone (type 1) or have an insulin receptor-mediated signaling pathway that is resistant to endogenous or exogenous insulin (type 2, or non-insulin-dependent diabetes mellitus (NIDDM)). Type 2 diabetes is the most common form of diabetes, affecting about 5% of individuals in the industrialized nations. In type 2 diabetics, major insulin-responsive tissues such as liver, skeletal muscle and fat exhibit the insulin resistance (Haring and Mehnert, *Diabetologia* 36:176–182 (1993); Haring et al., *Diabetologia*, 37 Suppl 2:S149–54 (1994)). The resistance to insulin in type 2 diabetes is complex and likely multifactorial but appears to be caused by an impaired signal from the insulin receptor to the glucose transport system and to glycogen synthase. Impairment of insulin receptor kinase has been implicated in the pathogenesis of this signaling defect. Insulin resistance is also found in many non-diabetic individuals, and may be an underlying etiologic factor in the development of the disease (Reaven, *Diabetes*, 37:1595–1607 (1988)).

Considerable information is known concerning the insulin receptor itself. The receptor consists of four separate subunits consisting of two identical α and two identical β-subunits. The β-subunits contain a tyrosine kinase activity and the ATP binding sites. The insulin receptor is activated by autophosphorylation of key tyrosine residues in its cytoplasmic tyrosine kinase domain. This autophosphorylation is required for subsequent activity of the insulin receptor. The autophosphorylation stabilizes the activated receptor kinase resulting in a phosphorylation cascade involving intracellular signaling proteins.

At present there are limited pharmacologic approaches to treatment of type 2 diabetes. Insulin is currently used as a treatment, but is disadvantageous because it must be injected. Although several peptide analogs of insulin have been described, none with a molecular weight below about 5000 daltons retains activity. Some peptides which interact with sites on the β-subunit of the insulin receptor have shown enhancement of the activity of insulin on its receptor (Kole et al., *J. Biol Chem.*, 271:31619–31626 (1996); Kasuya et al., *Biochem. Biophys. Res. Commun.*, 200:777–83 (1994)). Kohanski and others have reported on a variety of polycationic species that generate a basal effect, but do little to enhance insulin action (Kohanski, *J. Biol. Chem.*, 264:20984–91 (1989); Xu et al., Biochemistry 30:11811–19 (1991). These peptides apparently act on the cytoplasmic kinase domain of the insulin receptor.

In addition, certain non-peptide components have been found to enhance the agonist properties of peptide hormones, but none appear to act directly on insulin receptor kinase. For instance, the ability of thiazolidinediones, such as pioglitazone, to enhance adipocyte differentiation has been described (Kletzien, et al., *Mol. Pharmacol.*, 41:393 (1992)). These thiazolidinediones represent a class of potential anti-diabetic compounds that enhance the response of target tissues to insulin (Kobayashi, *Diabetes*, 41:476 (1992)). The thiazolidinediones switch on PPARγ, the nuclear transcription factor involved in adipocyte differentiation (Kliewer et al., *J. Bio. Chem,.* 170:12953 (1995)). Other anti-diabetic agents currently in use include both insulin secretagogues (such as the sulfonylureas) and biguanides (such as metformin) that inhibit hepatic glucose output. To date, non-peptide substances which can mimic the activating effect of insulin on the insulin receptor have eluded discovery.

Trimesic acid amides have been extensively studied. There are numerous citations regarding their use in polymers and polymer generation (e.g. U.S. Pat. No. 5,973,076, EP 940431A1), however, these compounds are generally highly lipophilic and do not have an acidic functionality appended onto them. Compounds with carboxylic acids as terminal groups are found to be useful as transition metal chelates for preparation of polymers (DE 4229182), rigid polyamide gels (*Polym. Mater. Sci. Eng.* (1992), 66, 154), and as coatings for aluminum and aluminum alloys (DE 3327191).

Some trimesic acid amide compounds have been found to have biological effects. Trimesic acid amides have been described as platelet aggregation inhibitors (JP 08333324A2) and anti-inflammatories (U.S. Pat. No. 5,750, 573, U.S. Ser. No. 184,540), but these compounds have a highly basic guanidine, amidine, or a unique amidinohydrazone or guanylhydrazone as terminating functionalities. Compounds with highly acidic terminal functional groups include (EP 741128A2, WO 96/14324A1) sulfate esters of aminosugars as cell migration and proliferation inhibitors, and multianionic compounds as complement inhibitors (U.S. Pat. No. 4,123,455).

A variety of polyanionic sulfonic acid derivatives including suramin, azo dyes and related compounds are known in the art and have been established as potential therapeutics for a variety of disease indications. Suramin, described in 1917, is a polysulfonic acid that has been extensively researched (Dressel, *J. Chem. Ed.*, 38:585 (1961); Dressel, *J. Chem. Ed.*, 39:320 (1962)). It has therapeutic uses as an antihelminthic and antiprotozoal. More recently, it has been described as an inhibitor of reverse transcriptase in certain avian and murine retroviruses (De Clercq, *Cancer Letter,* 8:9 (1979); Mitsuya et al., *Science,* 226:172 (1984)). Recent studies indicate that polyanionic suramin analogs have antiangiogenic, antiproliferative activity, and anti-viral activity (Gagliardi et al., Cancer Chemother. Pharmacol., 41:117 (1988); Doukas et al., Cancer Res., 55: 5161 (1995); Mohan et al., Antiviral Chem., 2:215 (1991)). A number of other substituted-hydroxy-naphthalenedisulfonic acids and bis-naphthylsulfonic acids have been described in the patent literature as complement inhibitors (U.S. Pat. Nos. 4,046, 805, 4,132,730, 4,129,591, 4,120,891, 4,102,917, 4,051, 176). However, the literature on the trimesic acid amides does not suggest that these compounds will be useful in the treatment of hyperglycemia or diabetes.

The documents referred to in this application, including Prov. App. No. 60/230,738, are incorporated herein by reference.

SUMMARY OF THE INVENTION

In a first aspect, this invention is compounds of formula I:

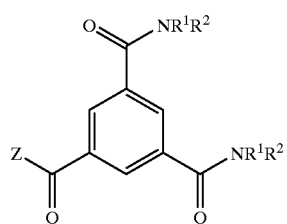

where:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R and R together with the conjoining nitrogen are C$_3$–C$_9$ heteroaryl, or C$_3$–C$_5$ heterocyclyl; and
Z is OH, Cl, Br, F, OR$^1$ or NR$^1$R$^2$ wherein R$^1$ and R$^2$ are as defined above;
and the pharmaceutically acceptable salts thereof,
as single stereoisomers or mixture of stereoisomers.

In a second aspect, this invention is pharmaceutical compositions comprising a therapeutically effective amount of a compound of Formula I, or a pharmaceutically acceptable salt thereof, as a single stereoisomer or mixture of stereoisomers thereof, and at least one pharmaceutically acceptable carrier.

The compounds of the first aspect of this invention and the compositions of the second aspect of this invention are useful for stimulating the kinase activity of the insulin receptor, activating the insulin receptor, enhancing the activation of the insulin receptor or enhancing glucose uptake into cells, and consequently are useful for the treatment of hyperglycemia, type 1 and type 2 diabetes.

In a third aspect, this invention is a method of stimulating the kinase activity of the insulin receptor comprising contacting the insulin receptor, or the kinase portion thereof, with a compound of Formula I, or a pharmaceutically acceptable salt thereof, as a single stereoisomer or mixture of stereoisomers thereof, in an amount sufficient to stimulate the kinase activity of the insulin receptor.

In a fourth aspect, this invention is a method of activating the insulin receptor or enhancing the activation of the insulin receptor by insulin, comprising contacting the insulin receptor, or the kinase portion thereof, with a compound of Formula I, or a pharmaceutically acceptable salt thereof, as a single stereoisomer or mixture of stereoisomers thereof, in an amount sufficient to activate the insulin receptor or enhance insulin's activation of the insulin receptor. Enhancement of insulin's ability to activate its receptor in a mammal may be effected by administering the compound of formula I, or a pharmaceutically acceptable salt thereof, or a single stereoisomer or mixture of stereoisomers thereof, to the mammal.

In a fifth aspect, this invention is a method of stimulating the uptake of glucose into cells which display the insulin receptor, comprising contacting the cells in the presence of insulin with a compound of Formula I, or a pharmaceutically acceptable salt thereof, as a single stereoisomer or mixture of stereoisomers thereof, or a pharmaceutical composition thereof, in an amount sufficient to stimulate the uptake of glucose into the cells. The uptake of glucose into cells in a mammal may be effected by administering the compound, or a pharmaceutical composition thereof, to the mammal.

In a sixth aspect, this invention is a method of treating hyperglycemia, type I diabetes, or type 2 diabetes in a mammal, such as a human, comprising administering a therapeutically effective amount of a compound of Formula i, or a pharmaceutically acceptable salt thereof, as a single stereoisomer or mixture of stereoisomers thereof, or a pharmaceutical composition thereof, to the mammal in need of such treatment. The method of treatment may also comprise co-administering insulin to the mammal.

In a seventh aspect, this invention is processes for the preparation of compounds of Formula I, or pharmaceutically acceptable salts thereof, or single stereoisomers or mixtures of stereoisomers thereof.

DETAILED DESCRIPTION OF THE INVENTION (a) Definitions:

"Alkyl", as in "alkyl" or "alkyloxy", means a $C_1$–$C_{20}$ monovalent hydrocarbyl moiety which may be linear, branched, or cyclic. "Lower alkyl", as in "lower alkyl", "halo-lower alkyl", "aryl(lower)alkyl", or "heteroaryl (lower)alkyl", means a $C_1$–$C_{10}$ alkyl. The term "lower alkyl" includes such moieties as methyl, ethyl, isopropyl, propyl, butyl, isobutyl, sec-butyl, tert-butyl, pentyl, hexyl, cyclopentyl, cyclopropylmethyl, cyclohexyl, or cyclohexylmethyl. $C_1$–$C_6$ lower alkyls are preferred.

A "substituted alkyl" or "substituted lower alkyl" is an alkyl or lower alkyl, respectively, which is typically mono-, di-, or trisubstituted with a moiety such as aryl, substituted aryl, heteroaryl, nitro, cyano, halo, —OR, —SR, —C(O)R, —OC(O)R, —C(O)OR, —NRR$^3$, —S(O)$_2$OR, —OS(O)$_2$R, —S(O)$_2$NRR$^3$, —NRS(O)$_2$R$^3$, —C(O)OR, —C(O)NRR$^3$, or —NRC(O)R$^3$, wherein R and R$^3$ are, independently, hydrogen, lower alkyl, substituted lower alkyl, aryl, substituted aryl, heteroaryl, heteroaryl(lower)alkyl, substituted aryl(lower)alkyl, or aryl(lower)alkyl. Substituted alkyls or substituted lower alkyls which are substituted with one to three of the substituents selected from the group consisting of cyano, halo, lower alkyloxy, thio, nitro, amino, or hydroxy are particularly preferred.

A "halo-lower alkyl" is a lower alkyl substituted with one to three halo groups, and is further exemplified by such radicals as —CH$_2$, Br, —CF$_3$, —CH$_2$CF$_3$ and —CH$_2$CCl$_3$.

"Aryl", as in "aryl", "aryloxy", and "aryl(lower)alkyl", means a radical derived from an aromatic hydrocarbon containing 6 to 20 ring carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g., biphenyl). The aryl is preferably $C_6$–$C_{16}$, more preferably $C_6$ to $C_{14}$, especially $C_6$ to $C_{12}$.

A "substituted aryl" is an aryl which is substituted, multiply or singly, with a moiety such as an alkyl, substituted alkyl, acetyl, aryl, substituted aryl, halo, cyano, nitro, —OR, —SR, —C(O)R, —OC(O)R, —NRR$^3$, —S(O)$_2$R, —S(O)$_2$OR, —OS(O)$_2$R, —S(O)$_2$NRR$^3$, —NRS(O)$_2$R$^3$, —C(O)OR, —C(O)NRR$^3$, tetrazolyl, or —NRC(O)R$^3$, wherein R and R$^3$ are, independently, hydrogen, lower alkyl, substituted lower alkyl, aryl, substituted aryl, heteroaryl, heteroaryl(lower)alkyl, aryl(lower)alkyl, or substituted aryl (lower)alkyl. A substituted aryl may be substituted from one to seven times with any combination of the radicals listed above. Preferably, however, the substituted aryl is mono-, di-, or trisubstituted. Preferred substituents on a substituted aryl are lower alkyl, halo-lower alkyl, halo, cyano, thio, nitro, amino, lower alkyloxy, and hydroxy. The radicals —S(O)$_2$R, —S(O)$_2$OR, —S(O)$_2$NRR$^3$, —C(O)OR, —C(O)NRR$^3$, and tetrazolyl wherein R and R$^3$ are, independently, hydrogen or a lower alkyl, are also preferred substituents on a substituted aryl of the present invention.

"Heteroaryl", as in heteroaryl and heteroaryl(lower)alkyl, means a radical derived from an aromatic hydrocarbon containing 5 to 14 ring atoms, 1 to 5 of which are hetero atoms chosen, independently, from N, O, or S, and includes monocyclic, condensed heterocyclic, and condensed carbocyclic and heterocyclic aromatic rings (e.g., thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, tetrazolyl, etc.).

A "substituted heteroaryl" may have from one to three substituents such as an alkyl, substituted alkyl, acetyl, halo, cyano, nitro, aryl, substituted aryl, —OR, —SR, —C(O)R, —OC(O)R, —NRR$^3$, —S(O)$_2$R, —S(O)$_2$OR, —OS(O)$_2$R, —S(O)$_2$NRR$^3$, —NRS(O)$_2$R$^3$, —C(O)OR, —C(O)NRR$^3$, —NRC(O)R$^3$, or tetrazolyl wherein R and R$^3$ are, independently, hydrogen, lower alkyl, substituted lower alkyl, aryl, substituted aryl, heteroaryl, heteroaryl(lower) alkyl, aryl(lower)alkyl, or substituted aryl(lower)alkyl. In addition, any two adjacent substituents on the heteroaryl may optionally together form a lower alkylenedioxy. Preferred substituents on a substituted heteroaryl are hydroxy, halo, lower alkyloxy, cyano, thio, nitro, lower alkyl, halo-lower alkyl, halo-lower alkyl, and amino.

"Heterocyclyl" means a radical derived from an aliphatic, cyclic hydrocarbon containing 5 to 14 ring atoms, 1 to 5 of which are hetero atoms chosen, independently, from N, O, or S. Monocyclic rings (e.g., tetrahydrofuranyl, tetrahydropyranyl, piperidinyl, etc.) are preferred.

A "substituted heterocyclyl" may have from one to three substituents, preferably substituents like an alkyl, substituted alkyl, halo, cyano, nitro, —OR, —SR, —C(O)R, —OC(O)R, —NRR$^3$, —S(O)$_2$OR, —OS(O)$_2$R, —S(O)$_2$NRR$^3$, —NRS(O)$_2$R$^3$, —C(O)OR, —C(O)NRR$^3$, or —NRC(O)R$^3$, wherein R and R$^3$ are, independently, hydrogen, lower alkyl, substituted alkyl, aryl, substituted aryl, heteroaryl, heteroaryl(lower)alkyl, aryl(lower)alkyl, or substituted aryl(lower)alkyl. Preferred substituents on a substituted heterocyclyl are lower alkyl, halo-lower alkyl, halo, cyano, thio, amino, lower alkyloxy, and hydroxy.

"Aryl(lower)alkyl" means a lower alkyl radical which is substituted with an aryl, as previously defined. A "substituted aryl(lower)alkyl" means an aryl(lower)alkyl radical having one to three substituents on the aryl portion or the alkyl portion of the radical, or both.

"Heteroaryl(lower)alkyl" means a lower alkyl radical which is substituted with a heteroaryl, as previously defined. A "substituted heteroaryl(lower)aryl" means a heteroaryl (lower)alkyl radical having one to three substituents on the heteroaryl portion or the alkyl portion of the radical, or both.

A "lower alkyloxy" means an —OR$^4$ radical, where R$^4$ is a lower alkyl.

"Lower alkenyl" means any branched or unbranched unsaturated $C_2$–$C_{10}$ group having the number of carbon atoms specified, or up to 10 carbon atoms if no limitation on the number of carbon atoms is specified; and having 1 or more double bonds in the group. Lower alkenyl is exemplified by ethenyl, propenyl, butenyl, pentenyl, and hexenyl, in their various isomeric forms, where the unsaturated bond(s) can be located anywhere in the group.

"Halo" means bromo, iodo, fluoro, or chloro.

A "non-interfering substituent" (as, for example, in the description of compounds of Formula IV, below) means a substituent which, when present on a given compound, does not substantially decrease or otherwise inhibit a particular, desired bioactivity of the compound, such as the ability of the compound to stimulate the kinase activity of the insulin receptor, to activate the insulin receptor, or to stimulate the uptake of glucose into cells displaying the insulin receptor. The presence of the non-interfering substituent should not detrimentally affect the bioactivity of the compound by more than about 30%. Preferably, the non-interfering substituent decreases the bioactivity of the compound by less than about 10%. Most preferably, the non-interfering substituent does not decrease the bioactivity of the compound to any detectable degree. However, the effect of the presence of the non-interfering substituent on the compound need not be neutral. For instance, the non-interfering substituent may optionally increase a particular bioactivity of the compound. Suitable non-interfering substituents include, but are not limited to, hydrogen, alkyl, substituted alkyl, cyano, halo, nitro, —SR$^5$, —OR$^5$, and —NR$^5$R$^6$, wherein R$^5$ and R$^6$ are, independently, hydrogen, lower alkyl, or substituted lower alkyl.

A "pharmaceutically acceptable salt" may be any salt derived the reaction of, or addition to, a compound of this invention with an inorganic or organic acid or an inorganic or organic base. The term "pharmaceutically acceptable anion" refers to the anion of an acid addition salt of a compound of this invention. The term "pharmaceutically acceptable cation" refers to a cation formed by reaction of a compound of this invention with a base. The salt and/or the anion or cation are chosen not to be biologically or otherwise undesirable.

"Stereoisomers" are compounds that have the same sequence of covalent bonds and differ in the relative disposition of their atoms in space.

"Inner salts" or "zwitterions" can be formed by transferring a proton from a carboxyl group in a compound onto a lone pair of electrons of a nitrogen atom in an amino group of the compound.

The term "asymmetric" refers to compounds which do not display identity among its constituents arranged on opposite sides of a plane.

An "activated" derivative refers to a reactive form of a compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to reaction with another reagent.

A "radiolabel" is a radioactive atom, radical, or compound. Radiolabeling constitutes introducing a radioactive isotope of an element into a compound in a quantity sufficient for analysis.

A "therapeutically effective amount" means that amount which, when administered to a mammal for treating a disease, is sufficient to effect such treatment for the disease.

"Treating" or "treatment" of a disease in a mammal includes one or more of:

(1) preventing the disease from occurring in a mammal which may be predisposed to the disease but does not yet experience or display symptoms of the disease, (2) inhibiting the disease, i.e., arresting its development, and (3) relieving the disease, i.e., causing regression of the disease.

The term "disease", in the context of the present invention, is intended to include hyperglycemia and diabetes (both Type I diabetes and Type II diabetes).

The "kinase portion thereof", with respect to the insulin receptor, means the cytoplasmic tyrosine kinase domain of the insulin receptor.

(b) Compounds of the Invention

The compounds of this invention are represented by formula I:

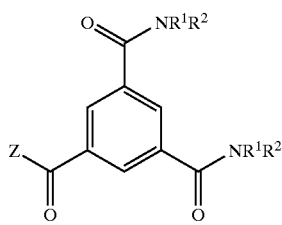

where:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl, and Z is OH, Cl, Br, F, OR$^1$ or NR$^1$R$^2$ wherein R$^1$ and R$^2$ are as defined above;
and the pharmaceutically acceptable salts thereof,
as single stereoisomers or mixture of stereoisomers.

Certain compounds of the invention may contain one or more chiral centers. In such cases, all stereoisomers also fall within the scope of this invention. The invention compounds include the individually isolated stereoisomers as well as mixtures of such stereoisomers.

It will be understood by one of ordinary skill in the art that the compounds may comprise a radioactive atom or atoms, capable of serving as a radiolabel to signal the presence of the compounds in assays and biological tissues, as may be useful, for example, in receptor assays, or in binding assays, or to track the distribution and metabolism of the compounds in an animal. Thus, the compounds include radiolabeled compounds.

Pharmaceutically acceptable salts of the compounds of the invention are also encompassed by the present invention and are useful in the methods and pharmaceutical compositions described herein.

Pharmaceutically acceptable salts include salts which may be formed when acidic protons present are capable of reacting with inorganic or organic bases. Typically the parent compound is treated with an excess of an alkaline reagent, such as hydroxide, carbonate or alkoxide, containing an appropriate cation. Cations such as Na$^+$, K$^+$, Ca$^{2+}$ and NH$_4^+$ are examples of cations present in pharmaceutically acceptable salts. The Na$^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as ethanolamine, diethanolamine, triethanolamine, N-methylglucamine, ethanolamine, and tromethamine.

If the compounds of the invention contain a basic group, an acid addition salt may be prepared. Acid addition salts of the compounds are prepared in a standard manner in a suitable solvent from the parent compound and an excess of acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenyipropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds form inner salts or zwitterions.

(c) Presently Preferred Embodiments

An embodiment of the invention is a compound of the formula:

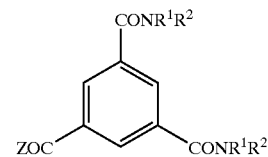

wherein:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl; and Z is OH, Cl, Br, F, OR$^1$ or NR$^1$R$^2$ wherein R$^1$ and R$^2$ are as defined above; wherein said compound is neither methyl 3-[(3,5-bis{N-[3,5-bis(methoxycarbonyl) phenyl]carbamoyl}phenyl)carbonyl-amino]-5-(methoxycarbonyl)-benzoate nor 5-({3,5-bis[N-(3,5-dicarboxyphenyl)carbamoyl]phenyl}-carbonylamino)benzene-1,3-dicarboxylic acid;

or a pharmaceutically acceptable salt thereof, or a single stereoisomer or mixture of stereoisomers thereof.

An additional embodiment of the invention is a compound of the formula:

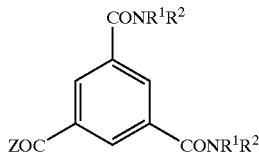

wherein:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl; and Z is OH, Cl, Br, F, OR$^1$ or NR$^1$R$^2$ wherein R$^1$ and R$^2$ are as defined above; wherein if Z is —NR$^1$R$^2$ and each R$^1$ is H and each R$^2$ is 3,5-dimethoxycarbonylphenyl or 3,5-dicarboxyphenyl, then the compound must be radiolabeled; or a pharmaceutically acceptable salt thereof, or a single stereoisomer or mixture of stereoisomers thereof.

Yet another embodiment of the invention is a compound of the formula:

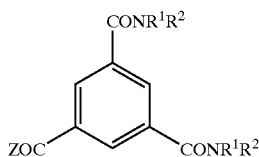

wherein:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl; and Z is OH, Cl, Br, F, OR$^1$ or NR$^1$R$^2$ wherein R$^1$ and R$^2$ are as defined above; wherein if Z is —NR$^1$R$^2$ and each R$^1$ (of CONR$^1$R$^2$, as in the structure depicted above) is H and each R$^2$ (of CONR$^1$R$^2$, as in the structure depicted above) is 3,5-dimethoxycarbonylphenyl or 3,5-dicarboxyphenyl, then the compound must be asymmetric;

or a pharmaceutically acceptable salt thereof, or a single stereoisomer or mixture of stereoisomers thereof.

A further embodiment of the invention is a compound of the formula:

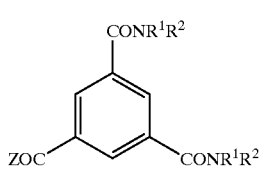

wherein:
R$^1$ and R$^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl; and Z is OH, Cl, Br, F, OR$^1$ or NR$^1$R$^2$ wherein R$^1$ and R$^2$ are as defined above;
wherein if each R$^1$ is H and each R$^2$ is 3,5-dimethoxycarbonylphenyl or 3,5-dicarboxyphenyl, then Z is different from NR$^1$R$^2$; or a pharmaceutically acceptable salt thereof, or a single stereoisomer or mixture of stereoisomers thereof.

An additional embodiment of the invention is a compound of the formula:

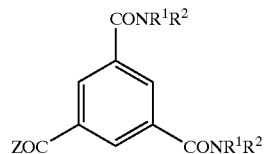

wherein:
R$^1$ and R$^2$ are, independently, hydrogen, lower alkyl, substituted lower alkyl, aryl, aryl substituted with a sulfo group, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or R$^1$ and R$^2$ together with the conjoining nitrogen are C$_3$–C$_9$ heteroaryl, or C$_3$–C$_5$ heterocyclyl; and Z is OH, Cl, Br, F, OR$^1$ or NR$^1$R$^2$ wherein R$^1$ and R$^2$ are as defined above; wherein said compound is neither methyl 3-[(3,5-bis{N-[3,5-bis(methoxycarbonyl)phenyl]carbamoyl}phenyl)carbonyl-amino]-5-(methoxycarbonyl)benzoate nor 5-({3,5-bis[N-(3,5-dicarboxyphenyl)carbamoyl]phenyl}carbonylamino)benzene-1,3-dicarboxylic acid;
or a pharmaceutically acceptable salt thereof, or a single stereoisomer or mixture of stereoisomers thereof.

In a more preferred embodiment of the preferred embodiments listed above, each R$^1$ is hydrogen.

Preferably, if R$^1$ or R$^2$ is aryl substituted with a sulfo group, the aryl is naphthyl. Also, preferably, if R$^1$ is phenyl, then the sulfo group is in the 2 position on R$^1$.

Preferably, the compounds of Formula I are defined as follows:

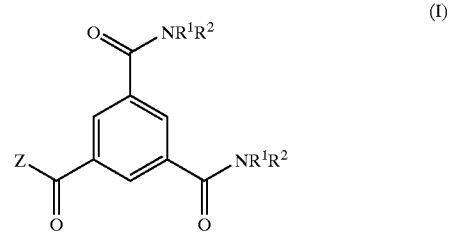

(I)

wherein each R$^1$ and R$^2$ of the compounds of Formula I are hydrogen and aryl or substituted aryl respectively; and Z is OH, Cl, Br, F, OR$^1$ or NR$^1$R$^2$, wherein R$^1$ and R$^2$ are as defined above; or a pharmaceutically acceptable salt thereof, or a single stereoisomer or mixture of stereoisomers thereof. The aryl or substituted aryl is preferably naphthyl or substituted naphthyl. Alternatively, the aryl or substituted aryl may be phenyl or substituted phenyl.

More preferably, Z is OH or NR¹R². More preferably still, Z is OH, R¹ is H, and R² is substituted aryl. More preferably still, R² is substituted naphthyl Most preferably, R² is naphthyl substituted with S(O)₂OH.

In another preferred embodiment, Z is NR¹R², R¹ is H, and R² is substituted aryl. More preferably, R² is substituted phenyl. More preferably still, R² is phenyl substituted with 1 or 2 SO₂OH or C(O)OR, wherein R is hydrogen or lower alkyl. Alternatively, R² is substituted naphthyl. More preferably, R² is naphthyl substituted with 1 or 2 SO₂OH or C(O)OR, wherein R is hydrogen or lower alkyl. Most preferably, R² is naphthyl substituted with SO₂OH.

Another preferred compound of Formula I is a compound of Formula II:

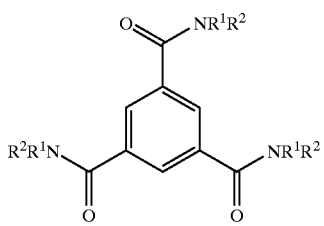

(II)

wherein each R¹ and R² of the compounds of Formula II are preferably hydrogen and aryl or substituted aryl respectively; or a pharmaceutically acceptable salt thereof, or a single stereoisomer or mixture of stereoisomers thereof. The aryl or substituted aryl is preferably naphthyl or substituted naphthyl. Alternatively, the aryl or substituted aryl may be phenyl or substituted phenyl.

Especially preferred compounds of Formula II are compounds of Formula III:

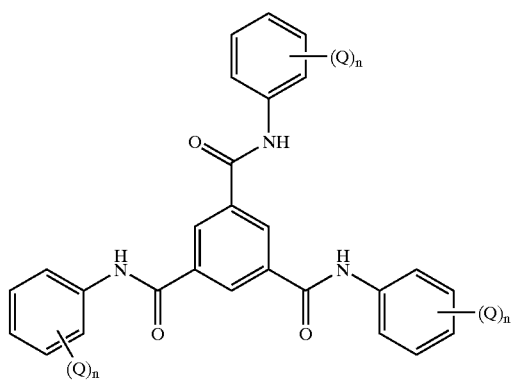

(III)

wherein each Q is independently defined as a non-interfering substituent: lower alkyl, substituted lower alkyl, acetyl, cyano, halo, nitro, —SR, —OR, —NRR', aryl, substituted aryl, —C(O)R, —C(O)OR, —C(O)NRR', —S(O)₂R, —S(O)₂NRR', —S(O)₂OR, heteroaryl, or substituted heteroaryl, where each R and R' is, independently, hydrogen, lower alkyl, or substituted lower alkyl; and n is 1–5; or a pharmaceutically acceptable salt thereof, or a single stereoisomer or mixture of stereoisomers thereof. Preferably each Q is —C(O)OR, —C(O)NRR', —S(O)₂R, —S(O)₂NRR', —S(O)₂OR, or tetrazolyl and n is equal to 1. The number of the non-interfering substituents depends on the spatial arrangements on the aryl ring (in this case, phenyl).

In a preferred embodiment of the invention, Q of the compounds of Formula III is —C(O)OR, —C(O)NRR', —S(O)₂OR, —S(O)₂NRR' or tetrazolyl. More preferably, Q is —S(O)₂OR or —S(O)₂NRR'. More preferably still, Q is —S(O)₂OH. In an alternative preferred embodiment, Q is, instead, —C(O)OH or tetrazolyl.

Examples of preferred compounds of Formula I include compounds of Formula IV:

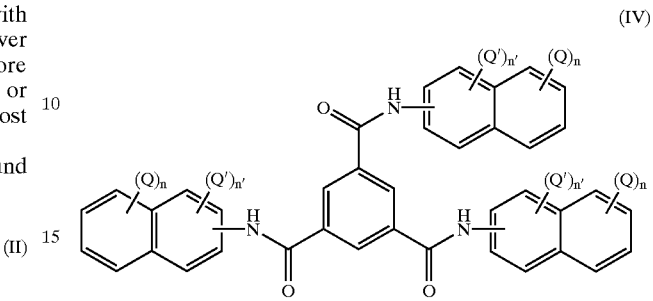

(IV)

wherein each Q and Q' is independently defined as a non-interfering substituent: lower alkyl, substituted lower alkyl, acetyl, cyano, halo, nitro, —SR, —OR, —NRR', aryl, substituted aryl, —C(O)R, —C(O)OR, —C(O)NRR', —S(O)₂R, —S(O)₂NRR', —S(O)₂OR, heteroaryl, or substituted heteroaryl, where each R and R' is, independently, hydrogen, lower alkyl, or substituted lower alkyl; and n and n' are independently 0, 1, 2, 3, 4, or 5; or a pharmaceutically acceptable salt thereof, or a single stereoisomer or mixture of stereoisomers thereof. Preferably each Q is —C(O)OR, —C(O)NRR', —S(O)₂R, —S(O)₂NRR', —S(O)₂OR, or tetrazolyl, wherein R and R' are as defined above. Preferably, n is equal to 1. The number of the non-interfering substituents depends on the spatial arrangements on the aryl ring (in this case, phenyl).

In a preferred embodiment of the invention, Q of the compounds of Formula IV is —C(O)OR, —C(O)NRR', —S(O)₂OR, —S(O)₂NRR' or tetrazolyl. More preferably, Q is —S(O)₂OR or —S(O)₂NRR'. More preferably still, Q is —S(O)₂OH. In an alternative preferred embodiment, Q is instead —C(O)OH or tetrazolyl. Most preferably, n is 1, Q is —S(O)₂OH, n' is 0–5 and Q' is a non-interfering substituent selected from the group consisting of lower alkyl, substituted lower alkyl, acetyl, cyano, halo, nitro, —SR, —OR, —NRR', aryl, substituted aryl, —C(O)R, —C(O)OR, —C(O)NRR', heteroaryl, or substituted heteroaryl, where each R and R' is, independently, hydrogen, lower alkyl, or substituted lower alkyl.

Other preferred compounds of Formula I include compounds of Formula V:

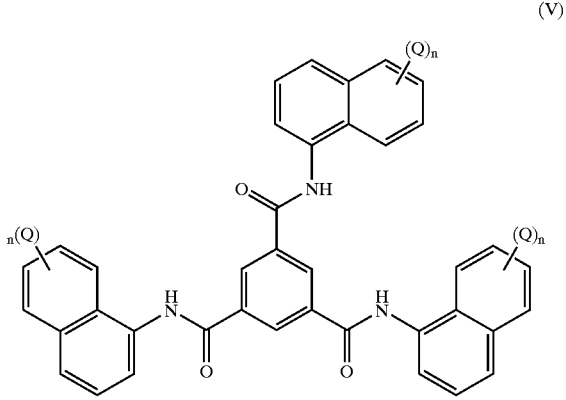

(V)

wherein each Q is independently defined as a non-interfering substituent: lower alkyl, substituted lower alkyl, acetyl, cyano, halo, nitro, —SR, —OR, —NRR', aryl, substituted aryl, —C(O)R, —C(O)OR, —C(O)NRR', —S(O)$_2$R, —S(O)$_2$NRR', —S(O)$_2$OR, heteroaryl, or substituted heteroaryl, where each R and R' is, independently, hydrogen, lower alkyl, or substituted lower alkyl; and n is 1–5; or a pharmaceutically acceptable salt thereof, or a single stereoisomer or mixture of stereoisomers thereof. Preferably each Q is —C(O)OR, —C(O)NRR', —S(O)$_2$R, —S(O)$_2$NRR', —S(O)$_2$OR, or tetrazolyl and n is equal to 1. The number of the non-interfering substituents depends on the spatial arrangements on the aryl ring (in this case, phenyl).

In a preferred embodiment of the invention, Q of the compounds of Formula V is —C(O)OR, —C(O)NRR', —S(O)$_2$OR, —S(O)$_2$NRR' or tetrazolyl. More preferably, Q is —S(O)$_2$OR, or —S(O)$_2$NRR'. More preferably still, Q is —S(O)$_2$OH. Most preferably, n is 1 and Q is —S(O)$_2$OH. In an alternative preferred embodiment, Q is instead —C(O)OH or tetrazolyl.

Compounds of the present invention which are suitable for use in pharmaceutical compositions and methods of the invention, include, but are not limited to the following compounds:

1) 4-({3,5-bis[N-(4-carboxyphenyl)carbamoyl]phenyl}carbonylamino)benzoic acid;
2) 5-({3,5-bis[N-(6-sulfonaphthyl)carbamoyl]phenyl}carbonylamino)naphthalene-2-sulfonic acid;
3) 4-({ 3,5-bis[N-(4-sulfophenyl)carbamoyl]phenyl}carbonylamino)benzenesulfonic acid;
4) 8-({3,5-bis[N-(7-sulfonaphthyl)carbamoyl]phenyl}carbonylamino)naphthalene-2-sulfonic acid;
5) 3,5-bis[N-(6-sulfonaphthyl)carbamoyl] benzoic acid;
6) 5-({3,5-bis[N-(5-sulfonaphthyl)carbamoyl]phenyl}carbonylamino)naphthalene-sulfonic acid;
7) 4-({3,5-bis[N-(4-sulfonaphthyl)carbamoyl]pheny}carbonylamino)naphthalene-sulfonic acid;
8) 2-({3,5-bis[N-(2-sulfophenyl)carbamoyl]phenyl}carbonylamino)benzenesulfonic acid;
9) 2-({3,5-bis[N-(1-sulfo(2-naphthyl))carbamoyl]phenyl}carbonylamino)naphthalene-sulfonic acid;
10) 3-({3,5-bis[N-(3-sulfophenyl)carbamoyl]phenyl}carbonylamino)benzenesulfonic acid;
11) 6-({3,5-bis[N-(6-sulfo(2-naphthyl))carbamoyl]phenyl}carbonylamino)naphthalene-2-sulfonic acid;
12) 6-({3,5-bis[N-(5-sulfo(2-naphthyl))carbamoyl]phenyl}carbonylamino)naphthalene-sulfonic acid;
13) 7-({3,5-bis[N-(7-sulfo(2-naphthyl))carbamoyl]phenyl}carbonylamino)naphthalene-2-sulfonic acid;
14) 2-({3,5-bis[N-(2-carboxyphenyl)carbamoyl]phenyl}carbonylamino)benzoic acid;
15) 8-({3,5-bis[N-(8-sulfonaphthyl)carbamoyl]phenyl}carbonylamino)naphthalene-sulfonic acid;
16) methyl 3-[(3,5-bis{N-[3,5-bis(methoxycarbonyl)phenyl]carbamoyl}phenyl)-carbonylamino]-5-(methoxycarbonyl)benzoate;
17) 4-{[(3,5-bis{N-[(4-carboxyphenyl)methyl]carbamoyl}phenyl)carbonylamino]-methyl}benzoic acid;
18) methyl 3-[(3,5-bis{N-[3-(methoxycarbonyl)phenyl]carbamoyl}phenyl)carbonyl-amino]benzoate;
19) methyl 4-({[3,5-bis(N-{[4-(methoxycarbonyl)phenyl]methyl}carbamoyl)phenyl]-carbonylamino}methyl)benzoate;
20) methyl 4-[(3,5-bis{N-[4-(methoxycarbonyl)phenyl]carbamoyl}phenyl)carbonyl-amino]benzoate;
21) 5-({3,5-bis[N-(3,5-dicarboxyphenyl)carbamoyl]phenyl}carbonylamino)benzene-1,3-dicarboxylic acid;
22) 3-({3,5-bis[N-(2,3-dicarboxyphenyl)carbamoyl]phenyl}carbonylamino)benzene-1,2-dicarboxylic acid;
23) methyl 2-[(3,5-bis{N-[2-(methoxycarbonyl)phenyl]carbamoyl}phenyl)carbonyl-amino]benzoate;

and the pharmaceutically acceptable salts thereof, as single stereoisomers or mixtures of stereoisomers.

The above-described and the above-named compounds are useful for stimulating insulin receptor kinase activity. This utility herein disclosed is novel and has not previously been described. However, the structures of compounds 16) and 21) listed above are disclosed in U.S. Pat. Nos. 4,123,455 and 4,159,384 to Conrow et al, in which they are said to be useful as complement inhibitors, inhibitors of a complex group of proteins involved in immune, allergic, and immunopathologic responses.

Syntheses and descriptions of the novel compounds and biological assays for the novel compounds are outlined in Example 1.

(d) Pharmacology and Utility:

Compounds of the invention have been found to bind to the kinase domain and stimulate autophosphorylation of the receptor (Example 2, below). In addition, these compounds have been shown to enhance insulin's ability to effect the transport of glucose into cultured adipocytes cells (Example 3, below).

The ability of compounds of the invention to stimulate autophosphorylation of the insulin receptor and to stimulate the uptake of glucose into cells which is demonstrated in the specific examples indicates their usefulness in the treatment and management of subjects with diabetes. Without intending to be bound by any theory, it is believed that the compounds of this invention act directly on the kinase function of the receptor and do not necessarily compete with insulin for binding at the insulin-binding site, nor do they effect activation of the receptor by a mechanism similar to that exhibited by insulin. Thus, they are directly able to activate the kinase to autophosphorylate, to potentiate the effect of insulin, to activate the kinase function of the receptor in phosphorylating exogenous substrates and to effect the increased uptake of glucose by adipocytes and insulin receptor-bearing cells in general and to lower blood glucose in diabetic subjects. Accordingly, by virtue of the activities of the compounds of the invention, they may be used to stimulate the kinase activity of an insulin receptor, to enhance the activation of the insulin receptor by insulin, to enhance the stimulation by insulin of cellular glucose uptake, and to stimulate the lowering of blood glucose in diabetic subjects. Thus, the compounds of this invention are useful in the treatment of diabetes.

More specifically, one of the methods of the invention is directed to a method of stimulating the kinase activity of the insulin receptor. This method comprises contacting the insulin receptor, or the kinase portion thereof, with a compound of the invention in an amount sufficient to stimulate the kinase activity of the insulin receptor. By stimulating the kinase activity of the insulin receptor, both autophosphorylation as well as the phosphorylation of exogenous substrates is enhanced. The stimulation of the kinase activity of the insulin receptor may occur either in vivo or in vitro.

In another method of the invention, the insulin receptor is activated by contacting the insulin receptor, or the kinase portion thereof, with a compound of the invention in an amount sufficient to stimulate insulin's activation of its receptor. The targeted insulin receptor may optionally be on the surface of a cell in a mammal. In such a case, the contacting is effected by administering the compound, or a pharmaceutical composition thereof, to the mammal.

In still another method of the invention, the compounds of the invention are used to stimulate the uptake of glucose into cells displaying the insulin receptor. This method comprises contacting the cells with a compound of the invention, optionally in the presence of insulin, and in an amount sufficient to stimulate the uptake of glucose into the cells. The targeted cells may optionally be in a mammal and the step of contacting the receptor with the compound may then be effected by administering the compound, or pharmaceutical composition thereof, to the mammal.

The invention also provides a method of treating hyperglycemia, types I and II diabetes in a mammal, preferably a human. The method of treating these conditions comprises administering a therapeutically effective amount of a compound of the invention, or a pharmaceutical composition thereof, to the mammal. Optionally, the method may further comprise treating the mammal with an additional form of therapy for hyperglycemia. For instance, the method may comprise administering a therapeutically effective amount of a compound of the invention, or a pharmaceutical composition thereof, to the mammal with insulin. The amount of insulin which is delivered to the mammal should be in a therapeutically effective amount when used in conjunction with a compound of the invention. However, the amount delivered to a mammal in conjunction with a compound of the invention is preferably less than an amount which would be therapeutically effective if delivered to the mammal alone. It is understood that the insulin which is administered in any of the treatments of the present invention may either be isolated from a natural source or recombinant. In addition, an insulin analog may be substituted for insulin in any of the treatments of the present invention.

The invention also provides a method of preparing a test compound which stimulates insulin receptor kinase activity, comprising
  (a) submitting a compound of Formula I to an assay of insulin receptor kinase stimulation and noting the results of the assay;
  (b) submitting a test compound to the assay and noting the results of the assay;
  (c) comparing the results of the assays, whereby a test compound which stimulates similar or greater insulin receptor kinase activity than the compound of Formula I in the assay is identified as a compound which stimulates insulin receptor kinase activity; and
  (d) preparing the identified compound by a method known per se.

The invention further provides a method of performing an assay, said assay comprising contacting an insulin receptor with a compound, the method comprising performing the assay with a radiolabeled compound of Formula I.

Any compound of the invention may be used in the methods of the invention. Thus, any compound of the invention may be used in the contacting step of the methods of the invention for stimulating autophosphorylation of the insulin receptor, for stimulating the uptake of glucose into cells, for stimulating the kinase activity of the insulin receptor, for activating the insulin receptor, for stimulating the uptake of glucose into cells displaying the insulin receptor, for stimulating the lowering of blood glucose in diabetic subjects, and in the administering step in the method of the invention for treating hyperglycemia, types I and II diabetes in a mammal. Preferred compounds for the practice of the methods of the invention are preferred compounds of this invention, such as compounds of Formula IV and Formula V, particularly those in which Q is —C(O)OR, —C(O)NRR', —S(O)$_2$OR, —S(O)$_2$NRR' or tetrazolyl.

Further, still more preferred compounds for the practice of the methods of the invention are compounds of Formula IV and V in which Q is —S(O)$_2$OH. The most preferred compounds for the practice of the methods of the invention are those compounds of Formula IV and V in which n is equal to 1 and Q is —S(O)$_2$OH. In an alternative preferred embodiment, Q is instead —C(O)OH or tetrazolyl.

The compounds of the invention may be used in the preparation of a medicament for the treatment of hyperglycemia, type I diabetes, or type II diabetes.

A radiolabeled form of a compound of the invention may be used as a diagnostic for identifying and/or obtaining compounds that have the function of stimulating the kinase activity of the insulin receptor, activating the insulin receptor, or stimulating the uptake of glucose in cells displaying the insulin receptor.

The compounds of the invention may additionally be used for validating, optimizing, or standardizing bioassays.

Certain compounds of the invention, such as, for example, the highly reactive acid halides, can be used as intermediates to prepare other compounds of the invention. Furthermore, certain compounds of the invention are useful as intermediates to prepare other compounds of the invention with higher activity.

(e) Administration and Pharmaceutical Compositions

The pharmaceutical compositions of the invention comprise a compound of Formula I and at least one pharmaceutically acceptable carrier. Preferably, the pharmaceutical composition may comprise a preferred compound of formula I, i.e., a compound of formula II, III, IV, or V as an active ingredient. Particularly preferred pharmaceutical compositions comprise compounds of Formula IV or Formula V, particularly those in which Q is —C(O)OR, —C(O)NRR', —S(O)$_2$OR, —S(O)$_2$NRR' or tetrazolyl. Further, still more preferred compounds for pharmaceutical compositions are compounds of Formula IV or V in which Q is —S(O)$_2$OH. The most preferred compounds for pharmaceutical compositions are those compounds of Formula IV or V in which n is equal to 1 and Q is —S(O)$_2$OH. In an alternative preferred embodiment, preferred pharmaceutical compositions comprise compounds of Formula IV or Formula V in which Q is instead —C(O)OH or tetrazolyl. However, pharmaceutical compositions which comprise any of the compounds of the invention are contemplated.

The method of treatment described in the previous section comprises the administration of an effective quantity of a compound of the invention, preferably dispersed in a pharmaceutical carrier. Dosage units of the active ingredient are generally selected from the range of 0.01 to 1000 mg/kg, preferably 0.01 to 100 mg/kg and more preferably 0.1 to 50 mg/kg, but will be readily determined by one skilled in the art depending upon the route of administration, age and condition of the patient. These dosage units may be administered one to ten times daily for acute or chronic disease. No unacceptable toxicological effects are expected when compounds of the invention are administered in accordance with the present invention.

One of ordinary skill in the art of treating such diseases will be able to ascertain a therapeutically effective amount of a compound of the invention for a given disease without undue experimentation and in reliance upon personal knowledge and the disclosure of this application. The compounds of the invention, or pharmaceutical compositions thereof, may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in A. Gennaro, ed., Remington: *The Science and Practice of Pharmacy*, 20th ed., Lippincott, Williams & Wilkins, Philadelphia, Pa.

Compositions can take the form of tablets, pills, capsules, semisolids, powders, sustained release formulations, solutions, suspensions, elixirs, aerosols, or any other appropriate composition and are comprised of, in general, a compound of the invention in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

The pharmaceutical compositions of this invention may also be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride or sodium citrate. Alternatively, these compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is use, the preparation will be in the form of a syrup, elixir, emulsion or an aqueous or non-aqueous suspension. Such a liquid formulation may be administered directly p.o. or filled into a soft gelatin capsule.

Some specific examples of suitable pharmaceutical compositions are described in Examples 4–6, below.

Typically, a pharmaceutical composition of the present invention would be packaged in a container with a label indicating use of the pharmaceutical composition in the treatment of hyperglycemia, type 1 diabetes, or type 2 diabetes, or a combination of the disease conditions.

(f) EXAMPLES

The compounds of the invention are prepared by conventional methods of organic chemistry.

Generally, a compound of the formula

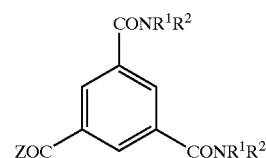

(I)

wherein:

$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl (lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl, and Z is OH, Cl, Br, F, $OR^1$ or $NR^1R^2$ wherein $R^1$ and $R^2$ are as defined above, or a pharmaceutically acceptable salt thereof, or a single stereoisomer or mixture of stereoisomers thereof;

may be prepared by a process comprising:

a) reaction of a 1,3,5-benzenetricarboxylic acid or an activated derivative thereof, with at least 1 to at least 3 moles $HNR^1R^2$ wherein $R^1$ and $R^2$ are as defined above;

(b) reaction of an activated carboxy di-amide of the formula

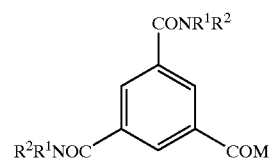

with a primary amine $R^1NH_2$ or a secondary amine $R^1R^2NH$ to form a tri-amide of Formula 1, wherein M is any substituent that will allow reaction with said amine, wherein $R^1$ and $R^2$ are as defined above; or (c) reaction of an activated dicarboxy-amide of the formula

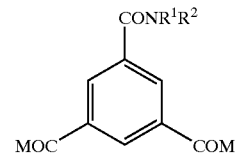

with a primary amine $R^1NH_2$ or a secondary amine $R^1R^2NH$ to form a tri-amide of Formula I, wherein M is any substituent that will allow reaction with said amine, wherein $R^1$ and $R^2$ are as defined above; or (d) esterification of a compound of the formula

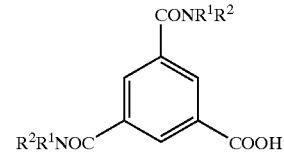

or an activated derivative thereof to form an ester of formula 1, wherein $R^1$ and $R^2$ are as defined above; or (e) hydrolysis of an ester of the formula

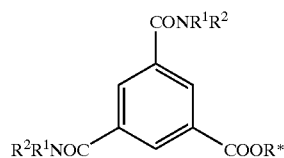

wherein $R^1$ and $R^2$ are as defined above and $R^*$ is $OR^1$ to form an acid or salt of a compound of Formula I; or (f) chemical elaboration of one or more substituents of substituted $R^1$ or $R^2$, wherein said substituent is convertible into another substituent; or (g) conversion of a compound of Formula I with three $NR^1R^2$ groups to a compound of Formula I with one or two $NR^1R^2$ groups, wherein $R^1$ and R are as defined above, or (h) conversion of the compound of Formula I to a pharmaceutically acceptable salt; or (i) conversion of a salt of the compound of Formula I to a free compound; or (j) conversion of a salt of the compound of Formula I to a pharmaceutically acceptable salt; or (k) resolution of a racemic mixture of any proportions of the compound of Formula I to yield a stereoisomer thereof.

Another example of the synthesis of compounds of Formula I proceeds according to the following reaction scheme:

where each of $R^{1a}$ and $R^{2a}$ are independently selected from $R^1$, and each of $R^{1b}$ and $R^{2b}$ are independently selected from $R^2$, as defined above, and Z is as defined above.

As shown above, a differentially protected, mono-methyl, mono-benzyl ester of benzenetricarboxylic acid may be converted to the mono-acid chloride using oxalyl chloride. Reaction with an amine affords a mono-amido compound. Selective saponification of the methyl ester under basic conditions, followed by an acidic workup will give another carboxylic acid which may be converted to the acid chloride using oxalyl chloride. Reaction with a second amine will now give a di-amido compound which may be asymmetric (i.e. $R^{1a} R^{2a}$ and/or $R^{1b} R^{2b}$). The final carboxylic ester may be converted to the carboxylic acid by more forcing saponification conditions, or by catalytic hydrogenolysis. After isolation of the carboxylic acid, one can covert the carboxylic acid into the acid halide and then react with a third reagent to give a compound of Formula I with potentially three different amido substituents. Other compounds where Z $NR^1R^2$ may be prepared from the carboxylic acid by standard organic syntheses.

In some cases, protective groups may be introduced and later removed. Suitable protective groups for amino, hydroxyl, carboxyl groups are described in Greene, et al., *Protective Groups in Organic Synthesis*, Second Edition, John Wiley and Sons, New York, 1991. Activation of carboxylic acids can be achieved by using a number of different reagents as described in Larock, *Comprehensive Organic Transformations*, VCH Publishers, New York, 1989.

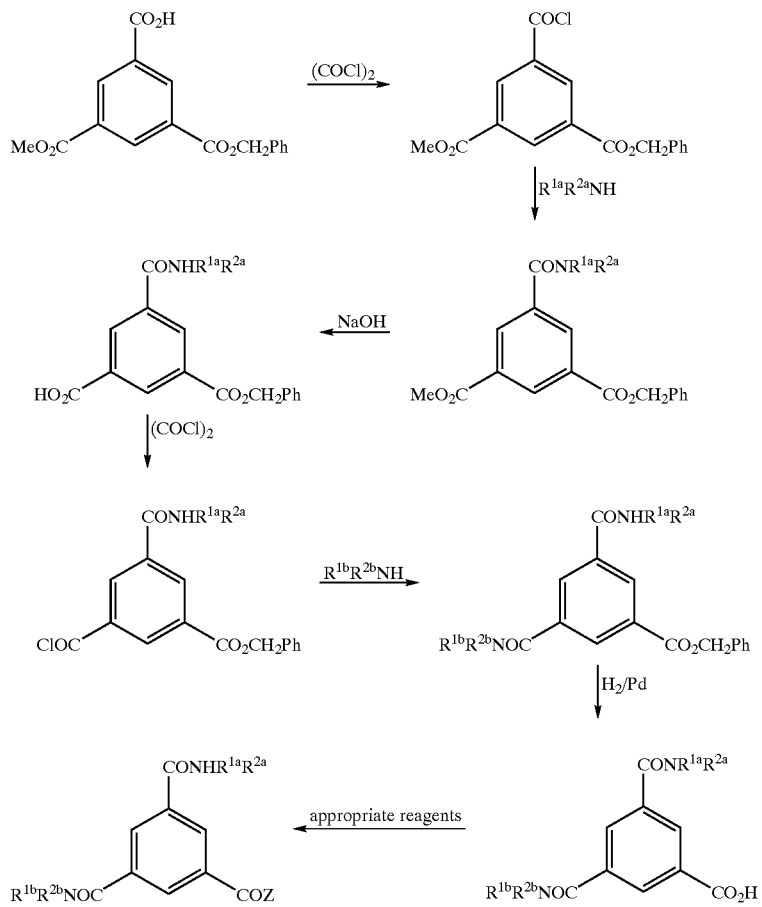

Specifically, the compounds of the invention can be synthesized as shown in the following examples or by modifying the exemplified syntheses by means known to those of ordinary skill in the art. For example, although the halogen of the 1,3,5-benzenetricarbonyl trihalide in the example below is Cl, it will be understood by those of skill in the art that any halogen, preferably Cl, Br or F, may be used in synthesizing the compounds of the invention.

Preparation of Benzenetricarboxylic Acid Derivatives

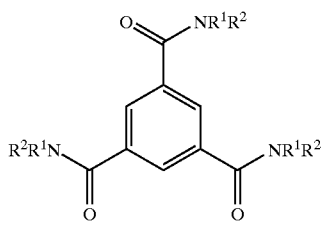

The symmetrical amide analogs were either prepared by Schotten-Baumann acylation of three equivalents of the amine component with 1,3,5-benzenetricarbonyl trichloride or by condensation of three equivalents of the amine component with 1,3,5-benzenetricarbonyl trichloride using catalytic 4-(dimethylamino)pyridine in methylene chloride/pyridine.

The Schotten-Baumann method was used for all sulfonic acid containing aromatic amines as well as aromatic amines containing a single carboxylic acid moiety. The 4-(dimethylamino)pyridine catalyzed procedure was used for all other amines.

One synthetic route according to the present invention is outlined in Reaction Scheme I, below:

Reaction Scheme I

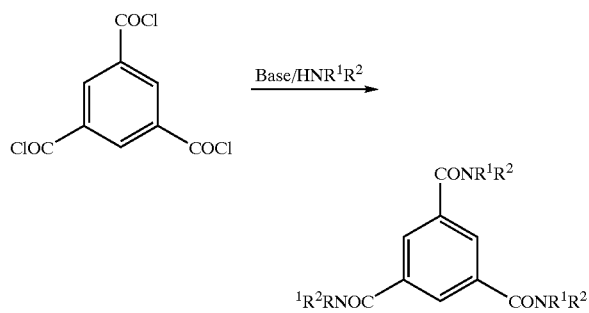

Example 1

General Method A (Schoften-Baumann Procedure)

A solution of 1,3,5-benzenetricarbonyl trichloride (1.9 mmol) in 1,4-dioxane (5 mL) was added slowly over about 10 minutes to an ice-cooled stirred solution (or suspension) of the amine component (11.3 mmol) in aqueous 1 N sodium hydroxide (15 mL). During the addition the pH was maintained at >5 by the careful addition of aqueous 1 N sodium hydroxide. The reaction mixture was stirred for 1 hour at 0° C. then allowed to come to room temperature.

The products were purified by individual methods, dependent on the structure of the amine component.

The product can be precipitated out of the reaction mixture and purified either by washing with dilute hydrochloric acid or by preparative reverse phase HPLC, e.g., 4-({3,5-bis[N-(4-carboxyphenyl)carbamoyl]phenyl}carbonylamino)benzoic acid, 1.

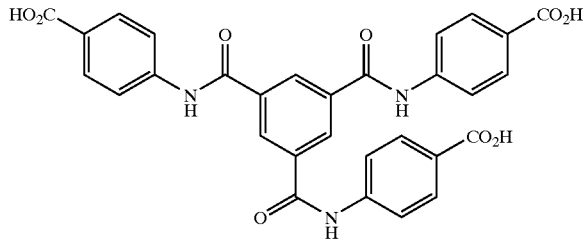

$^1$H NMR: δ10.92 (3H, s), 8.77 (3H, s), 7.98 (12H, s)

Alternatively, the product was purified from the lyophilized reaction mixture either by dissolution in water and precipitation with acetone or by preparative reverse phase HPLC, e.g., 8-({3,5-bis[N-(7-sulfonaphthyl)carbamoyl]phenyl}carbonylamino)-naphthalene-2-sulfonic acid, 4.

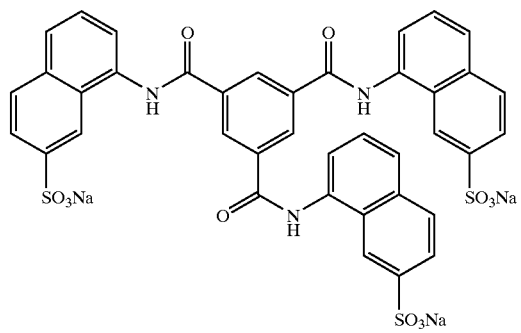

$^1$H NMR: δ11.04 (3H, s), 8.92 (3H, s) 8.35 (3H, s), 7.91 (3H, d, J=8.5 Hz), 7,85 (3H, d, J=7.8 Hz), 7.74 (3H, d, J=8.6 Hz), 7.55 (6H, m)

The products from 3- or 4-aminobenzenesulfonic acid (metanilic or sulfanilic acid), were purified from the lyophilized reaction mixture either by dissolution in water and precipitation with acetone or by simple washing with water, e.g., 4-({3,5-bis[N-(4-sulfophenyl))carbamoyl]phenyl}carbonylamino) benzenesulfonic acid, 7

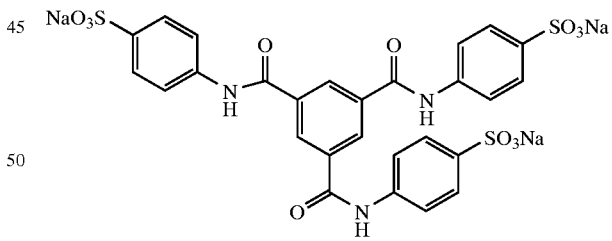

$^1$H NMR: δ10.64 (3H, s), 8.72 (3H, s), 7.76 (6H, d, J=8.6 Hz), 7.60(6H, d, J=8.6 Hz). The product derived from 2-aminobenzenesulfonic acid (aniline-2-sulfonic acid) precipitated from the reaction mixture and no purification was needed.

Preparation of 1,3,5-benzenetricarboxylic acid derivatives in which Z is not $NR^1R^2$ are easily accessible to one skilled in the art.

The bisamide product in which only two amines were incorporated into the trimesic acid scaffold (derived from 5-aminonaphthalene-2-sulfonic acid) was prepared in an analogous manner to that described for the corresponding triamide derivatives, except that only 2 equivalents of 5-aminonaphthalene-2-sulfonic acid were used. The product was isolated directly from the reaction mixture by precipitation on adjusting the pH to about 2 with 1 M hydrochloric acid.

In addition, further modification may be performed on a bisamide product. For example, compound 5 (Z=OH) could be modified further at the free carboxylic acid function to introduce a different amide group (reaction with an amine) or an ester group (reaction with an alcohol) after appropriate activation of the carboxylic acid group. For example, treatment of compound 5, with thionyl chloride would lead to Z=Cl. Alternatively, treatment of compound 5, with thionyl chloride followed by addition of methanol in methylene chloride and subsequent purification, would lead to an ester with Z=OMe. In a similar manner, an amine may be substituted for the alcohol to lead to new amides. It will be understood by one of ordinary skill in the art, having knowledge of synthetic methods and of the compounds desired, that these reactions may, or may not, require manipulation of protecting groups of the remaining reactive functionalities.

In general the method of using only two equivalents of amine would produce a compound analogous to 5 and again modification of the free carboxylic acid could produce compounds in which Z is not $NR^1R^2$ but could be generated from a different amine or a phenol. As before, this may, or may not, require manipulation of protecting groups on the remaining reactive functionalities.

The solvent for all NMR data was $d_6$-methyl sulfoxide. The analytical data for the synthesized compounds are shown in Table A, below.

TABLE A

| Compound # | $^1$H NMR Data | MS Data (m/z key fragment) |
|---|---|---|
| 1 | 7.98 (12H, s), 8.77 (3H, s), 10.92 (3H, s) | NT |
| 2 | 7.61 (3H, t, J=7.7 Hz), 7.68 (3H, d, J=6.8 Hz), 7.77 (3H, dd, J=1.5 Hz, J=8.8 Hz), 7.95 (3H, d, J=8.5 Hz), 8.05 (3H, d, J=8.9 Hz), 8.21 (3H, s), 8.98 (3H, s), 10.84 (3H, s) | NT |
| 3 | 7.60 (6H, d, J=8.6 Hz), 7.76 60 (6H, d, J=8.6 Hz), 8.72 (3H, s), 10.64 (3H, s) | NT |
| 4 | 7.55–7.65 (6H, m), 7.74 (3H, d, J=8.6 Hz), 7.85 (3H, d, J=7.8 Hz), 7.91 (3H, d, J=8.5 Hz), 8.35 (3H, s), 8.92 (3H, s), 11.04 (3H, s) | NT |
| 5 | 7.57–7.64 (4H, m), 7.75 (2H, d, J=7.2 Hz), 7.78–8.02 (4H, m), 8.21 (2H, s), 8.87 (2H, s), 9.01 (1H, s), 10.85 (2H, s), 13.4–14.0 (1H, br. s) | 309 |

TABLE A-continued

| Compound # | $^1$H NMR Data | MS Data (m/z key fragment) |
|---|---|---|
| 6 | 7.48–7.64 (9H, m), 7.99 (3H, d, J=7.0 Hz), 8.10 (3H, d, J=8.4 Hz), 8.84 (3H, d, J=8.2 Hz), 8.99 (3H, s), 10.82 (3H, s) | NT |
| 7 | 7.54–7.62 (9H, m), 8.01 (3H, d, J=7.7 Hz), 8.12 (3H, m), 8.92 (3H, m), 9.03 (3H, s), 10.91 (3H, s) | NT |
| 8 | 7.16 (3H, t, J=7.6 Hz), 7.44 (3H, t, J=7.1 Hz), 7.75 (3H, d, J=7.8 Hz), 8.52 (3H, d, J=8.3 Hz), 8.68 (3H, s), 11.72 (3H, s) | NT |
| 9 | 7.03 (3H, d, J=8.9 Hz), 7.23 (3H, t, J=7.4 Hz), 7.37 (3H, t, J=8.1 Hz), 7.67 (6H, d, J=8.4 Hz), 8.64 (6H, s), 8.77 (3H, d, J=8.8 Hz) | NT |
| 10 | 7.30–7.41 (6H, m). 7.88 (3H, dd, J=2.0 Hz, J=7.3 Hz), 8.07 (3H, s), 8.74 (3H, s), 10.62 (3H, s) | NT |
| 11 | 7.69 (3H, d, J=8.4 Hz), 7.84 (3H, d, J=8.7 Hz), 7.94–8.03 (6H, m), 8.20 (3H, s), 8.53 (3H, s), 8.87 (3H, s), 10.92 (3H, s) | NT |
| 12 | 7.42 (3H, t, J=7.7 Hz), 7.86–7.90 (9H, m), 8.53 (3H, d, J=2.0 Hz), 8.82 (3H, d, J=9.4 Hz), 8.69 (3H, s), 10.84 (3H, s) | NT |
| 13 | 7.65 (3H, d, J=8.5 Hz), 7.85 (3H, d, J=8.7 Hz), 7.93 (3H, d, J=9.2 Hz), 8.07 (3H, s), 8.14 (3H, dd, J=1.8 Hz, J=8.9 Hz), 8.62 (3H, s), 9.01 (3H, s) 11.24 (3H, s) | NT |
| 14 | 7.27 (3H, m), 7.69 (3H, m), 8.06 (3H, d, J=8.0 Hz), 8.68 (3H, d, J=8.3 Hz), 8.82 (3H, m), 12.49 (3H, s) | NT |
| 15 | 7.43 (3H, t, J=7.7 Hz), 7.58 (3H, t, J=7.9 Hz), 7.82 (3H, d, J=7.3 Hz), 7.99 (3H, d, J=7.2 Hz), 8.15 (3H, d, J=6.5 Hz), 8.25 (3H, dd, J=1.4 Hz, J=7.4 Hz), 8.60 (3H, s), 12.76 (3H, s) | NT |
| 16 | NT | 783 |
| 17 | NT | 609 |
| 18 | NT | 609 |
| 19 | NT | 651 |
| 20 | NT | 609 |
| 21 | NT | 699 |
| 22 | NT | 699 |
| 23 | NT | 609 |

All preparative HPLC purifications used a 250×20mm ID, 5 μm column (YMC, ODS-AQ). The mobile phases were (A) 95% water, 5% acetonitrile containing 0.05% trifluoroacetic acid and (B) 5% water, 95% acetonitrile containing 0.05% trifluoroacetic acid. Detection was with UV light at 254 nm.

The formulae of the compounds given in Table A above are as follows:

TABLE B

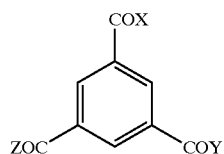

| Compound | X | Y | Z |
|---|---|---|---|
| 1 | (4-carboxyphenyl)amino | (4-carboxyphenyl)amino | (4-carboxyphenyl)amino |
| 2 | (6-sulfonaphthyl)amino | (6-sulfonaphthyl)amino | (6-sulfonaphthyl)amino |
| 3 | (4-sulfophenyl)amino | (4-sulfophenyl)amino | (4-sulfophenyl)amino |
| 4 | (7-sulfonaphthyl)amino | (7-sulfonaphthyl)amino | (7-sulfonaphthyl)amino |

TABLE B-continued

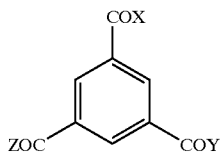

| Compound | X | Y | Z |
|---|---|---|---|
| 5 | (6-sulfonaphthyl)amino | (6-sulfonaphthyl)amino | OH |
| 6 | (5-sulfonaphthyl)amino | (5-sulfonaphthyl)amino | (5-sulfonaphthyl)amino |
| 7 | (4-sulfonaphthyl)amino | (4-sulfonaphthyl)amino | (4-sulfonaphthyl)amino |
| 8 | (2-sulfophenyl)amino | (2-sulfophenyl)amino | (2-sulfophenyl)amino |
| 9 | (4-sulfo-3-naphthyl)amino | (4-sulfo-3-naphthyl)amino | (4-sulfo-3-naphthyl)amino |
| 10 | (3-sulfophenyl)amino | (3-sulfophenyl)amino | (3-sulfophenyl)amino |
| 11 | (6-sulfo-2-naphthyl)amino | (6-sulfo-2-naphthyl)amino | (6-sulfo-2-naphthyl)amino |
| 12 | (8-sulfo-3-naphthyl)amino | (8-sulfo-3-naphthyl)amino | (8-sulfo-3-naphthyl)amino |
| 13 | (7-sulfo-2-naphthyl)amino | (7-sulfo-2-naphthyl)amino | (7-sulfo-2-naphthyl)amino |
| 14 | (2-carboxyphenyl)amino | (2-carboxyphenyl)amino | (2-carboxyphenyl)amino |
| 15 | (8-sulfonaphthyl)amino | (8-sulfonaphthyl)amino | (8-sulfonaphthyl)amino |
| 16 | (3,5-dimethoxycarbonyl phenyl)amino | (3,5-dimethoxycarbonyl phenyl)amino | (3,5-dimethoxycarbonyl phenyl)amino |
| 17 | (4-carboxyphenyl) methylamino | (4-carboxyphenyl) methylamino | (4-carboxyphenyl) methylamino |
| 18 | (3-methoxycarbonyl phenyl) amino | (3-methoxycarbonyl phenyl) amino | (3-methoxycarbonyl phenyl) amino |
| 19 | (4-methoxycarbonyl phenyl) methylamino | (4-methoxycarbonyl phenyl) methylamino | (4-methoxycarbonyl phenyl) methylamino |
| 20 | (4-methoxycarbonyl phenyl) amino | (4-methoxycarbonyl phenyl) amino | (4-methoxycarbonyl phenyl) amino |
| 21 | (3,5-dicarboxyphenyl)amino | (3,5-dicarboxyphenyl)amino | (3,5-dicarboxyphenyl)amino |
| 22 | (2,3-dicarboxyphenyl)amino | (2,3-dicarboxyphenyl)amino | (2,3-dicarboxyphenyl)amino |
| 23 | (2-methoxycarbonyl phenyl) amino | (2-methoxycarbonyl phenyl) amino | (2-methoxycarbonyl phenyl) amino |

Example 2

$^{32}$P-cytoplasmic Kinase Domain (CKD) Autophosphorylation Assay

The complete β-kinase domain of the human insulin receptor (CKD) was expressed in, and purified from, baculovirus. CKD (4.0 μg/ml), in a solution of 29 mM HEPES (pH 7.6), 0.05% Triton X-100, 10 mM MgCl$_2$, 2 mM MnCl$_2$ (50 μl final volume), was combined with 50 μM ATP, and 5 μCi $^{32}$P-ATP (3000 Ci/mmol.). A test compound, or the vehicle (DMSO), was added to a final DMSO concentration of 1%. The mixture was incubated for 10 minutes at room temperature. The reaction was terminated by the addition of 10 μl of 200 mM EDTA. A 30 μl volume was removed, mixed with 5 μl of 6× Laemmeli sodium dodecyl sulfate (SDS) treatment buffer, and heated to 95° C. for 5 minutes. A 20 μl aliquot was then run on an SDS-PAGE gel. The radioactivity incorporated into the CKD band is quantified by phosphorimaging of the gel, or scintillation counting of the excised bands.

The results for this assay are shown in Table 1. The potency of a compound for increasing phosphorylation is expressed as a percentage of the vehicle level. Compounds showing activities at 100% or lower were not tested at sufficiently high concentrations to demonstrate an effect.

TABLE 1

CKD phosphorylation

| Compound | CKD |
|---|---|
| 1 | 103.7 |
| 2 | 136.8 |
| 3 | 98.9 |
| 4 | 134.9 |
| 5 | 115.6 |
| 6 | 122.7 |
| 7 | 114.1 |
| 8 | 113.2 |
| 9 | 98.8 |
| 10 | 92.0 |
| 11 | 148.2 |
| 12 | 136.6 |
| 13 | 125.5 |
| 14 | 105.3 |
| 15 | 156.0 |
| 16 | 83.7 |
| 17 | 90.4 |
| 18 | 94.54 |
| 19 | 104.0 |
| 20 | 77.4 |
| 21 | 97.8 |
| 22 | 118.1 |
| 23 | 87.4 |

Example 3

Glucose Transport Activity

3T3 L1 fibroblasts (ATCC) were grown in Dulbecco's modified Eagie's medium (DMEM) with 10% fetal bovine serum (FBS). The cells were plated at a density of $3 \times 10^4$ cells/well in 24-well plates. Two days after confluence was reached, the cells were treated for 3 days with 0.5 nM isobutylmethylxanthine (IBMX), 1 μM dexamethasone, and 1.7 μM insulin. The cells were then transferred to DMEM with 10% fresh bovine serum with 1.7 μM insulin for 2 more days. The cells were maintained in DMEM with 10% FBS for an additional 4 days. Finally the cells were serum starved overnight in 0.1% bovine serum albumin (BSA) in DMEM prior to exposure to the test compounds.

The following day, the medium was replaced with 150 mM NaCl, 1.7 mM KCl, 0.9 mM $CaCl_2$, $K_2HPO_4$ (pH 7.4) to which was added either the experimental compounds, or their vehicle (DMSO). Insulin or its vehicle (0.01% BSA) was diluted in the assay buffer (containing test compound or vehicle, respectively) to a final concentration of 5.6 nM. After incubation for 30 min at 37° C., 0.5 μCi/ml of $^{14}C$-2-deoxy-D-glucose was added, and the incubation was continued for additional 30 min at 37° C. The cells were then washed 3 times with ice-cold PBS/20 mM glucose and lysed in 250 μl of lysis buffer (50 mM HEPES pH 7.6, 1% Triton X-100) for 30 min at room temperature. Radioactivity in the lysate was quantified by scintillation counting.

Once $^{14}C$-2-deoxy-D-glucose is transported into the cell it is not released. Glucose transport is, therefore, proportional to the amount of radioactivity in the lysate. The concentration of compound necessary to produce an increase in glucose transport greater than the sum of the standard deviation of the vehicle control plus the largest standard deviation of a test sample (generally 150% of the vehicle control) was recorded as the EC (effective concentration) The results of the glucose transport activity assay are shown in Table 2,

TABLE 2

| Glucose Transport | |
|---|---|
| Compound | EC (μM) |
| 1 | 3.2 |
| 2 | 3.2 |
| 3 | 3.2 |
| 4 | 3.2 |
| 5 | 10 |
| 6 | 3.2 |
| 7 | 3.2 |
| 8 | 3.2 |
| 9 | NT |
| 10 | 3.2 |
| 11 | NT |
| 12 | 3.2 |
| 13 | NT |
| 14 | NT |
| 15 | 3.2 |
| 16 | 1.6 |
| 17 | 3.2 |
| 18 | 3.2 |
| 19 | NT |
| 20 | 3.2 |
| 21 | 3.2 |
| 22 | 3.2 |
| 23 | 1.6 |

NT = Not tested above 3.2 μM

Example 4

Oral Pharmaceutical Composition Preparation— Solid Dosage Formulation

A pharmaceutical composition for oral administration may be prepared by combining the following:

| | % w/w |
|---|---|
| Compound of the invention | 10% |
| Magnesium stearate | 0.5% |
| Starch | 2.0% |
| Hydroxypropylmethylcellulose | 1.0% |
| Microcrystalline cellulose | 86.5% |

The mixture may be compressed to tablets, or filled into hard gelatin capsules.

The tablet may be coated by applying a suspension of film former (e.g. HPM cellulose), pigment (e.g. titanium dioxide) and plasticizer (e.g. diethyl phthalate) and drying the film by evaporation of the solvent. The film coat can comprise 2.0% to 6.0% of the tablet weight, preferably about 3.0%.

Example 5

Oral Pharmaceutical Composition Preparation— Capsule

A pharmaceutical composition of a compound of the invention suitable for oral administration may also be prepared by combining the following:

| | % w/w |
|---|---|
| Compound of the invention | 20% |
| Polyethylene glycol | 80% |

The medicinal compound is dispersed or dissolved in the liquid carrier, with a thickening agent added, if required. The formulation is then enclosed in a soft gelatin capsule by suitable technology.

Example 6

Pharmaceutical Composition for Parenteral Administration

A pharmaceutical composition for parenteral administration may be prepared by combining the following:

| | Preferred Level |
|---|---|
| Compound of formula I–VIII | 1.0% |
| Saline | 99.0% |

The solution is sterilized and sealed in sterile containers.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What we claim is:
1. A compound of the formula:

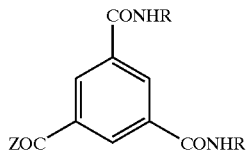

wherein:

R is naphthyl or substituted naphthyl; and

Z is OH, Cl, Br, F, or $OR^1$ or $NR^1R^2$ wherein $R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl;

or a pharmaceutically acceptable salt thereof, as a single stereoisomer or mixture of stereoisomers thereof.

2. The compound of claim 1, wherein Z is OH or $NR^1R^2$.
3. The compound of claim 2, wherein Z is OH.
4. The compound of claim 3, wherein R is a substituted naphthyl.
5. The compound of claim 4, wherein R is a naphthyl substituted with $S(O)_2OH$.
6. The compound of claim 2, wherein Z is $NR^1R^2$, $R^1$ is hydrogen and $R^2$ is a substituted aryl.
7. The compound of claim 6, wherein $R^2$ a substituted naphthyl.
8. The compound of claim 7, wherein R and $R^2$ are naphthyl substituted with one or two —$S(O)_2OH$ or —C(O)OR' wherein R' is hydrogen or a lower alkyl.
9. The compound of claim 8, wherein R and $R^2$ are naphthyl substituted with one or two —$S(O)_2OH$.
10. The compound of claim 1 selected from the group consisting of 5-({3,5-bis[N-(6-sulfonaphthyl) carbamoyl] phenyl}carbonylamino)naphthalene-2-sulfonic acid, 8-({3,5-bis[N-(7-sulfonaphthyl)carbamoyl] phenyl}carbonylamino)naphthalene-2-sulfonic acid, 5-({3,5-bis[N-(5-sulfonaphthyl)carbamoyl] phenyl}carbonylamino)naphthalenesulfonic acid, 4-({3,5-bis[N-(4-sulfonaphthyl)carbamoyl] phenyl}carbonylamino)naphthalenesulfonic acid, 2-({3,5-bis[N-(1-sulfo(2-naphthyl)) carbamoyl] phenyl}carbonylamino)naphthalene-sulfonic acid, 6-({3,5-bis[N-(6-sulfo(2-naphthyl))carbamoyl] phenyl}carbonylamino)naphthalene-2-sulfonic acid, 6-({3,5-bis[N-(5-sulfo(2-naphthyl))carbamoyl] phenyl}carbonylamino)naphthalene-sulfonic acid, 7-({3,5-bis[N-(7-sulfo(2-naphthyl))carbamoyl] phenyl}carbonylamino)naphthalene-2-sulfonic acid, and 8-({3,5-bis[N-(8-sulfonaphthyl)carbamoyl] phenyl}carbonylamino)naphthalenesulfonic acid.

11. A compound of the formula

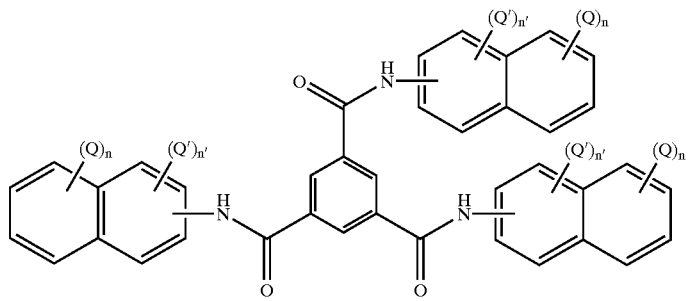

wherein each Q and Q' is a non-interfering substituent independently selected from the group consisting of lower alkyl, substituted lower alkyl, acetyl, cyano, halo, intro, —SR, —OR, —NRR', aryl, substituted aryl, —C(O)R, —C(O)OR, —C(O)NRR', —$S(O)_2R$, —$S(O)_2NRR'$, —$S(O)_2OR$, heteroaryl, and substituted heteroaryl, where each R and R' is, independently, hydrogen, lower alkyl, or substituted lower alkyl; and n and n' are independently integers of 0 through 5; or a pharmaceutically acceptable salt thereof, as a single stereoisomer or mixture of stereoisomers thereof.

12. The compound of claim 11, wherein Q is —C(O)OR, —C(O)NRR', —$S(O)_2R$, —$S(O)_2NRR'$, —$S(O)_2OR$, or tetrazolyl.

13. The compound of claim 12, wherein n is 1.
14. The compound of claim 13, wherein Q is —$S(O)_2NRR'$ or —$S(O)_2OR$.
15. The compound of claim 14, wherein Q is —$S(O)_2OH$.
16. The compound of claim 13, wherein Q is —C(O)OH or tetrazolyl.
17. A pharmaceutical composition comprising a compound of claim 1 and at least one pharmaceutically acceptable carrier.
18. A method of treatment of a mammal suffering from hyperglycemia, type 1 diabetes, or type 2 diabetes, comprising administering a therapeutically effective amount of a compound of claim 1 or a pharmaceutical composition containing such compound to a mammal in need of such treatment.
19. The method of claim 18 further comprising administering an additional form of therapy for hyperglycemia, type 1 diabetes, or type 2 diabetes to a mammal in need of the treatment.
20. The method of claim 19, wherein said additional form of therapy comprises a therapeutically effective amount of insulin.

21. The method of claim 20, wherein the therapeutically effective amount of insulin is a lesser amount than a therapeutically effective amount of insulin required when insulin is administered alone.

22. The method of claim 18, wherein said mammal is a human.

23. A method of treatment of a mammal suffering from hyperglycemia, type 1 diabetes, or type 2 diabetes, comprising administering a therapeutically effective amount of a compound of the formula:

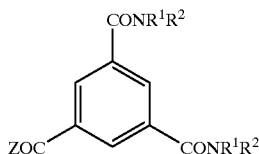

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR^1R^2$ wherein $R^1$ and $R^2$ are as defined above; or a pharmaceutically acceptable salt thereof, as a single stereoisomer or mixture of stereoisomers thereof, or a pharmaceutical composition containing such compound, to a mammal in need of such treatment.

24. The method of claim 23 further comprising administering an additional form of therapy for hyperglycemia, type 1 diabetes, or type 2 diabetes to a mammal in need of the treatment.

25. The method of claim 24, wherein said additional form of therapy comprises a therapeutically effective amount of insulin.

26. The method of claim 25, wherein the therapeutically effective amount of insulin is a lesser amount than a therapeutically effective amount of insulin required when insulin is administered alone.

27. The method of claim 23, wherein said mammal is a human.

28. A method of preparing a test compound which stimulates insulin receptor kinase activity, comprising (a) submitting a compound of the formula:

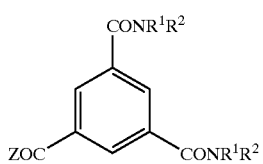

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR^1R^2$ wherein $R^1$ and $R^2$ are as defined above; or a pharmaceutically acceptable salt thereof, as a single stereoisomer or mixture of stereoisomers thereof, to an assay of insulin receptor kinase stimulation and noting the results of the assay;

(b) submitting a test compound to the assay and noting the results of the assay;

(c) comparing the results of the assays, whereby a test compound which stimulates similar or greater insulin receptor kinase activity than the compound tested in (a) above is identified as a compound which stimulates insulin receptor kinase activity; and (d) preparing the identified compound by a method known per se.

29. A method of performing an assay, said assay comprising contacting an insulin receptor with a compound, the method comprising performing the assay with a compound of the formula:

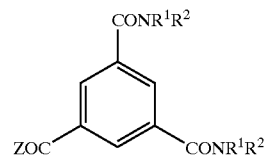

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, OR or $NR^1R^2$ wherein $R^1$ and $R^2$ are as defined above; or a pharmaceutically acceptable salt thereof, as a single stereoisomer or mixture of stereoisomers thereof.

30. A method of claim 29, where the compound is radiolabeled.

31. A method of stimulating the kinase activity of the insulin receptor in vivo or in vitro, comprising contacting the insulin receptor, or the kinase portion thereof, with a compound of the formula:

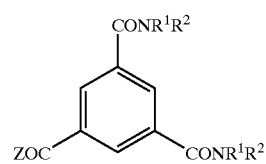

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR^1R^2$ wherein $R^1$ and $R^2$ are as defined above;

or a pharmaceutically acceptable salt thereof, as a single stereoisomer or mixture of stereoisomers thereof,
in an amount sufficient to stimulate the kinase activity of the insulin receptor.

32. A method of activating the insulin receptor, comprising contacting the insulin receptor, or the kinase portion thereof, with a compound of the formula:

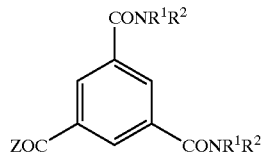

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR_1R^2$ wherein $R^1$ and $R^2$ are as defined above;
or a pharmaceutically acceptable salt thereof, as a single stereoisomer or mixture of stereoisomers thereof,
in an amount sufficient to stimulate insulin's activation of its receptor.

33. A method of activating the insulin receptor, comprising contacting the insulin receptor on the surface of a mammalian cell, or the kinase portion thereof, with a compound of the formula:

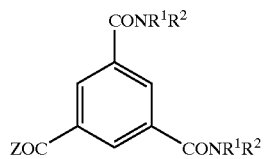

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR^1R^2$ wherein $R^1$ and $R^2$ are as defined above; or a pharmaceutically acceptable salt thereof, as a single stereoisomer or mixture of stereoisomers thereof,
in an amount sufficient to stimulate insulin's activation of its receptor.

34. A method of stimulating glucose uptake in cells displaying insulin receptors, comprising contacting the cells with a compound of the formula:

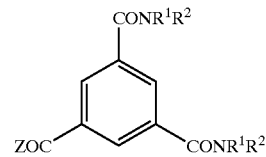

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, OR or $NR^1R^2$ wherein $R^1$ and $R^2$ are as defined above; or a pharmaceutically acceptable salt thereof, as a single stereoisomer or mixture of stereoisomers thereof,
in an amount sufficient to stimulate the uptake of glucose into the cells, optionally in the presence of insulin.

35. A method of stimulating glucose uptake in mammalian cells displaying insulin receptors, comprising contacting the cells with a compound of the formula:

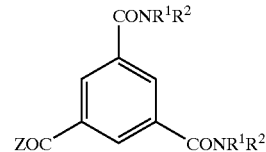

wherein:
$R^1$ and $R^2$ are, independently, hydrogen, lower alkyl, substituted lower alkyl, aryl, substituted aryl, heteroaryl, substituted heteroaryl, heterocyclyl, substituted heterocyclyl, aryl(lower)alkyl, substituted aryl(lower)alkyl, heteroaryl(lower)alkyl, substituted heteroaryl(lower)alkyl, or lower alkenyl, or $R^1$ and $R^2$ together with the conjoining nitrogen are $C_3$–$C_9$ heteroaryl, or $C_3$–$C_5$ heterocyclyl; and Z is OH, Cl, Br, F, $OR^1$ or $NR^1R^2$ wherein $R^1$ and $R^2$ are as defined above; or a pharmaceutically acceptable salt thereof, as a single stereoisomer or mixture of stereoisomers thereof,
or a pharmaceutical composition containing such compound,
in an amount sufficient to stimulate the uptake of glucose into the cells, optionally in the presence of insulin.

* * * * *